(12) United States Patent
Krieg et al.

(10) Patent No.: US 6,554,784 B1
(45) Date of Patent: Apr. 29, 2003

(54) APPARATUS AND METHOD FOR STABILIZING PELVIC RING DISRUPTION

(75) Inventors: James C. Krieg, Portland, OR (US); William B. Long, Portland, OR (US); Steven M. Madey, Lake Oswego, OR (US); Michael Bottlang, Portland, OR (US)

(73) Assignee: Legacy Emanuel Hospital & Medical Health Center, Portland, OR (US)

( * ) Notice: Subject to any disclaimer, the term of this patent is extended or adjusted under 35 U.S.C. 154(b) by 0 days.

(21) Appl. No.: 09/639,544

(22) Filed: Aug. 16, 2000

Related U.S. Application Data
(60) Provisional application No. 60/183,623, filed on Feb. 18, 2000.

(51) Int. Cl.$^7$ .................................................. A61F 5/00
(52) U.S. Cl. ............................ 602/23; 602/5; 128/99.1
(58) Field of Search ........................ 602/5, 19, 23–24, 602/32, 36, 38, 39, 60–64; 128/876, 845, 869, 875, 99.1, 100.1, 101.1; 2/311, 312, 321, 322, 336, 337; 24/68 R, 205; 188/31, 77 R; 601/41, 106; 482/93, 92, 106

(56) References Cited

U.S. PATENT DOCUMENTS

| | | | |
|---|---|---|---|
| 35,038 A | * 4/1862 | Pierce | |
| 2,552,475 A | 5/1951 | Austlid | |
| 4,715,364 A | 12/1987 | Noguchi | |
| 4,912,813 A | * 4/1990 | Muller et al. | 24/68 |
| 5,407,422 A | 4/1995 | Matthijs et al. | |
| 5,437,618 A | 8/1995 | Sikes | |
| 5,588,186 A | * 12/1996 | Ko | 24/585 |
| 5,647,824 A | * 7/1997 | Levenson | 482/92 |
| 5,690,122 A | 11/1997 | Weber-Unger | |
| 5,782,781 A | 7/1998 | Nagaoka | |
| 5,913,410 A | 6/1999 | Tsuchiya | |
| 6,066,109 A | * 5/2000 | Buser et al. | 602/23 |
| 6,099,490 A | * 8/2000 | Turtzp | 602/19 |

* cited by examiner

*Primary Examiner*—Denise M. Pothier
(74) *Attorney, Agent, or Firm*—Kolisch Hartwell, P.C.

(57) ABSTRACT

A pelvic sling device is provided for reducing a fractured pelvis. The device includes a belt member and a buckle component that automatically locks at an optimal predetermined tension level to provide distributed hoop-like compression and reduction for a fractured pelvis.

7 Claims, 7 Drawing Sheets

APPARATUS AND METHOD FOR STABILIZING PELVIC RING DISRUPTION

CROSS-REFERENCES TO RELATED APPLICATION

This application claims priority from U.S. Provisional Patent Application Serial No. 60/183,623, filed Feb. 18, 2000, which is hereby incorporated by reference.

FIELD OF THE INVENTION

The invention relates to emergency treatment of a fractured pelvis. In particular, the invention provides a non-invasive sling device for reducing a fractured pelvis in a manner that minimizes internal bleeding.

BACKGROUND OF THE INVENTION

Many people die from internal bleeding due to a fractured pelvis. Achieving rapid hemodynamic stability in patients who have a fractured pelvis decreases the mortality rate substantially. Unfortunately, currently there is no satisfactory method or device that may readily be utilized to stabilize a fractured pelvis in emergency situations outside a hospital. Pelvic stabilization at an emergency site within the first hour after the fracture occurs is critical and may often determine whether the patient lives or dies.

Reduction and stabilization of the pelvis is thought to be the most effective means to control bleeding for the following reasons. First, it decreases fracture fragment motion to prevent dislodgment of hemostatic clots and further tissue damage. Second, fracture reduction reopposes bleeding osseous surfaces, thus decreasing blood loss. Third, reduction decreases pelvic volume, thereby tamponading hemorrhage from the fracture and retroperitoneal tissue. Despite these widely recognized benefits, no adequate pelvic stabilization device for early management of pelvic fractures is currently available.

The current standard of care for treating pelvic trauma consists of fluid resuscitation, including appropriate use of blood products, angiography if necessary, and early invasive or non-invasive pelvic stabilization. Non-invasive pelvic stabilization techniques have been used. For example, a sheet may be wrapped around the pelvis and tied. Alternatively, a vacuum-type splinting device, or a pneumatic anti-shock garment may be used. These non-invasive techniques have a number of significant problems. One problem is that successful use and application of the device is quite dependent on the emergency caregiver. The person applying the device may not know how much compressive force to apply circumferentially around the pelvis. If too much force is applied, then the pelvis may be overly compressed causing significant complications. On the other hand, insufficient compressive force may leave the fractured pelvis unreduced, and therefore fail to adequately control internal bleeding.

Another problem with non-invasive pelvic stabilization devices that are currently used is that they typically prohibit or restrict vital access to the abdomen, perineum, and lower extremity. Furthermore, prolonged application of devices such as the pneumatic anti-shock garment has been associated with significant complications, such as compartment syndrome of the lower limbs.

Invasive pelvic stabilization methods utilize external fixation, pelvic C-clamps, and open reduction and subsequent internal fixation. External fixation devices can effectively reduce and stabilize the pelvis and are relatively simple to apply. However, their utility is limited most commonly to the operating room setting. The invasive pelvic stabilization methods generally are not appropriate for application at an emergency scene where unstable pelvic ring disruptions require rapid pelvic reduction and temporary stabilization.

Open reduction and internal fixation is the ultimate form of treatment for a fractured pelvis, and is considered the gold standard for accuracy of reduction, protection of neurovascular structures, and rigidity of fixation. However, its invasive nature makes it inappropriate for use in an emergency situation, such as the scene of a car accident, on the side of a mountain, or at a remote location of a traumatic fall.

Accordingly, an object of the invention is to provide a method and apparatus for pelvic reduction and stabilization that is non-invasive.

Another object is to provide a method and apparatus for pelvic reduction and stabilization that is capable of even and incremental application of hoop stress to both hemi-pelves while avoiding reactive forces that potentially can decrease the quality of reduction.

Another object of the invention is to provide a method and apparatus for pelvic reduction and stabilization that applies and maintains hoop stress around the pelvis at a preset and safe level, while avoiding the application of excessive hoop stress.

A further object of the invention is to provide a method and apparatus for stabilization of a fractured pelvis that can be applied in a rapid and simple manner by a single person without extensive training.

Still another object of the invention is to provide a method and apparatus for stabilizing a fractured pelvis that can be applied at an emergency site without the need for additional complex or heavy equipment.

Another object of the invention is to provide a method and apparatus for stabilizing a fractured hip in a nonintrusive manner, while allowing vital access to conduct other important emergency procedures on the patient.

Another object of the invention is to provide a method and apparatus that permits stable pelvic reduction prior to and during the application of a pelvic external fixator in the clinical setting.

SUMMARY OF THE INVENTION

The invention provides beneficial methods and apparatus for stabilizing a fractured pelvis in an emergency setting without requiring use of complex or invasive equipment. The invention may be used and carried out by a single person without extensive training or expertise.

The invention provides a sling device for stabilizing a fractured pelvis. A buckle is connected to a strap member to form a closed loop. The buckle has at least one automatic locking mechanism that allows the strap member to be tightened around a fractured pelvis until a predetermined threshold force is reached. The closed loop then maintains a substantially constant circumference until the strap member is released from the buckle.

The invention also provides a sling device including a belt member with two end portions. A buckle has two substantially identical belt-engaging mechanisms. Each belt engaging mechanism is configured to receive an end portion of the belt member so that the belt member can be tightened symmetrically around a person's pelvis by pulling on the end portions of the belt member simultaneously.

In a preferred embodiment of the invention, the belt member is secured with a buckle including at least one rotating cylinder. The rotating cylinder has an outer surface that contacts a portion of the belt member that at least partially wraps around the cylinder. The belt portion frictionally grips the outer surface of the cylinder so that when rotation of the cylinder is locked, the belt member is prevented from slipping over the outer surface of the immobilized cylinder.

The invention also provides a method of stabilizing a fractured pelvis. First, a belt is secured around a person's fractured pelvis. The tension of the belt is then automatically set at a level that has been predetermined to substantially reduce a fracture pelvis without excessive compression. In a preferred embodiment of the invention, the tension level of the belt is automatically set in the range of approximately 150 N to 250 N.

The invention also includes a method of securing a pelvic fixator in an emergency situation. The fractured pelvis is first temporarily stabilized by tightening a belt device around the pelvis. A pelvic fixator may subsequently be applied while the belt is secured around the person's pelvis.

DESCRIPTION OF THE INVENTION

The invention includes many aspects that may be employed advantageously to stabilize a fractured pelvis in an emergency situation. Generally, the invention employs a compressive device that can be easily applied to a patient to provide an appropriate level of hoop stress so that the fractured pelvis is reduced but not overly compressed. Preferred examples and embodiments of the invention are described below with reference to the figures.

Figure 1:
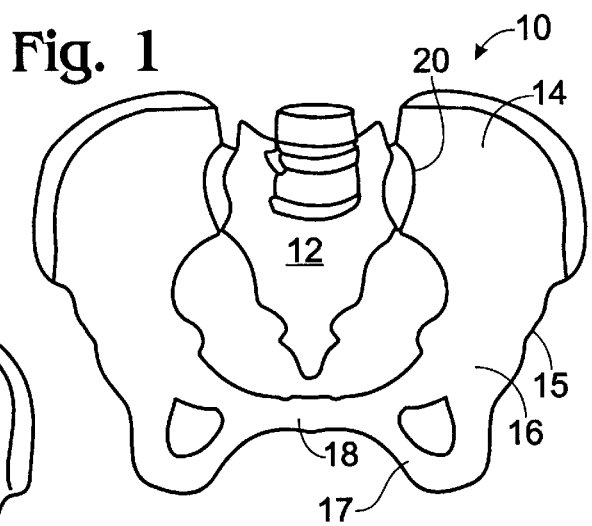
FIG. 1 is a front view of the pelvic ring.

FIG. 1 shows the bone structure that is referred to as the pelvic ring 10. The pelvic ring is formed by the sacrum 12, ilium 14, acetabulum 15, ischium 16, pubic rami 17, and symphysis pubis 18. Anteriorly, pelvic ring 10 contains a fibro cartilage joint. Posteriorly, the pelvic ring 10 contains the sacroiliac joints 20, which connect the sacrum 12 with the left and right ilium.

Figure 2A:
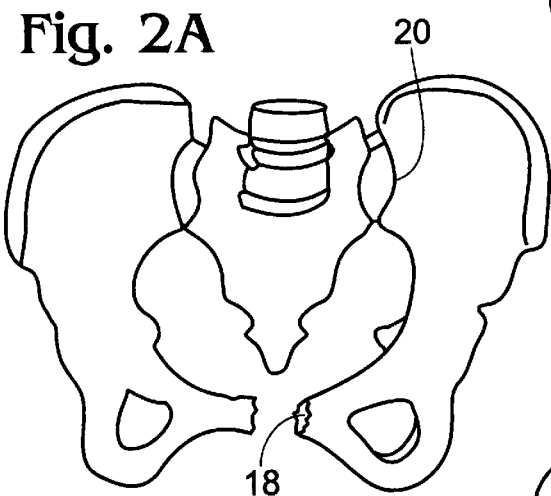
FIGS. 2A and 2B are front views of unstable pelvic ring disruptions.
Figure 2B:
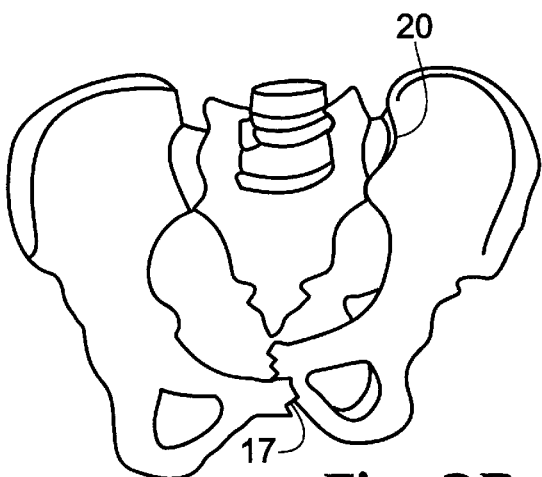

Unstable pelvic ring disruptions are usually manifested by two or more fracture sites. In an "open book" fracture, as shown in FIG. 2A, pelvic ring disruption is evident at symphysis pubis 18 and at one or both sacroiliac joints 20. FIG. 2B illustrates a lateral compression fracture in which pelvic ring disruption occurs at pubic rami 17 and at sacroiliac joint 20.

Figure 3:
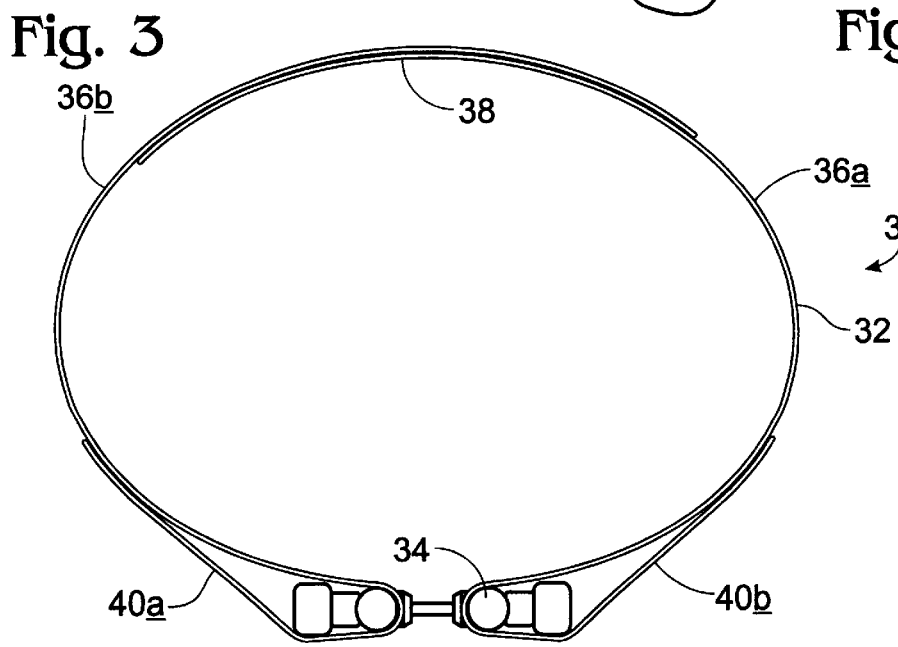
FIG. 3 is a top view of a pelvic sling device according to a preferred embodiment of the invention.

FIG. 3 shows a top view of a sling 30 including a belt member 32 operatively combined with buckle device 34. Belt member 32 is comprised of two overlapping lateral portions 36a and 36b. Belt portions 36a and 36b have a variably overlapping region 38 for making gross adjustments to the circumference of the sling so that one sling device can be used on people of different sizes. Any appropriate mechanism may be used to provide variable overlap fixation of lateral belt portions 36a and 36b, for example, hook and loop type fasteners, for example, VELCRO™, may be utilized in overlapping region 38.

Figure 5:
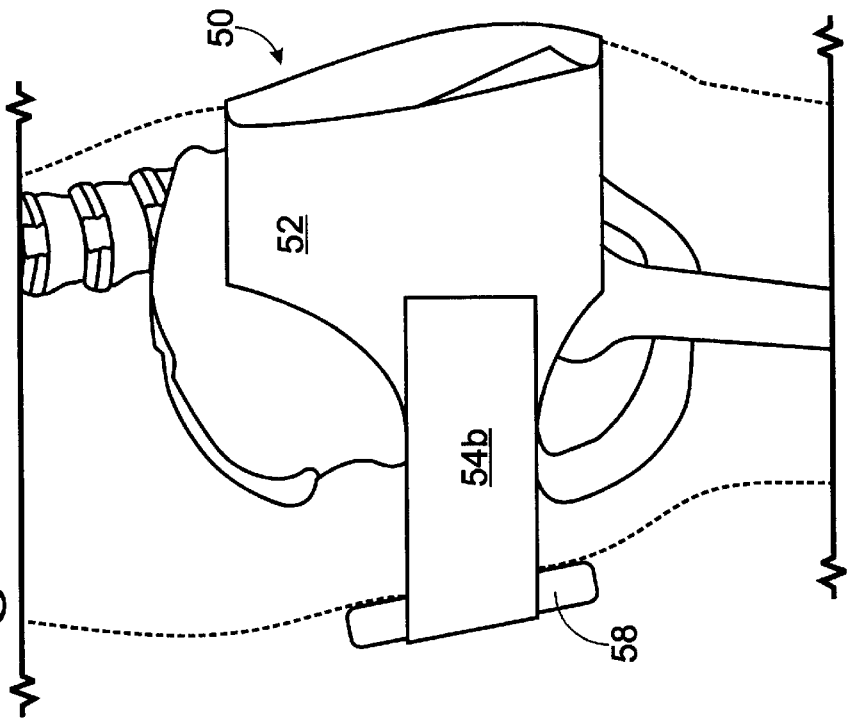
FIG. 5 is a side view of the sling and hipbone structure shown in FIG. 4.
Figure 4:
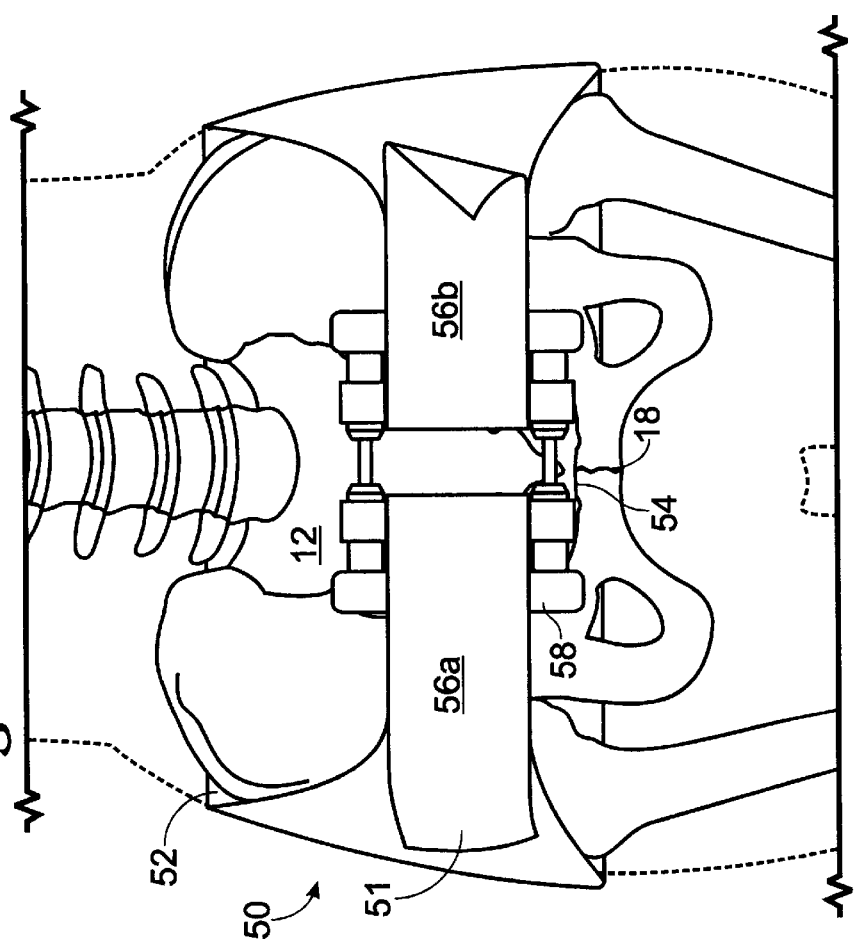
FIG. 4 is a front view of a pelvic sling applied to a fractured hip.

FIG. 4 is a front view of a pelvic sling shown in operative association with a human pelvis. FIG. 5 shows a side view of the same sling and pelvis of FIG. 4. Pelvic sling 50 has a belt portion 51 including an approximately 6-inch wide posterior sling component 52. Posterior sling component 52 is situated behind sacrum 12 with its lower edge located at the level of the superior rim 54 of symphysis pubis 18. Posterior sling component 52 is preferably made of a radiolucent material that is cushioned toward the skin interface to ensure a high degree of pressure distribution. The material is of sufficient stiffness to transmit tensile forces of at least 200 N without exhibiting strain larger than 10%. The material also has sufficient inherent elasticity to conform in part to body geometry. Posterior sling component 52 extends laterally toward the anterior portion of the abdomen. Symmetrical sling extensions 56a and 56b gradually decrease in width to approximately 2-inches as they circumvent the sides of the pelvis. The centerline of sling extensions 56a and 56b is approximately 2-inches above the lower edge of posterior sling component 52. Sling extensions 56a and 56b are directed through buckle 58 which is centered over the abdomen. Buckle 58 reverses the direction of both sling extensions 56a and 56b. Simultaneous application of sideward direct tensile force to each sling extension 56a and 56b yields in tensioning of the entire sling, which in turn induces even hoop stress around the pelvis. The hoop-stress subsequently reduces the geometric integrity of the disrupted pelvic ring and promotes stability of the fracture fragments. After application of sling tension at the appropriate level, the ends of sling extensions 56a and 56b are attached to lateral sling portions, for example, by hook and loop fasteners, to maintain sling tension.

Figure 6:
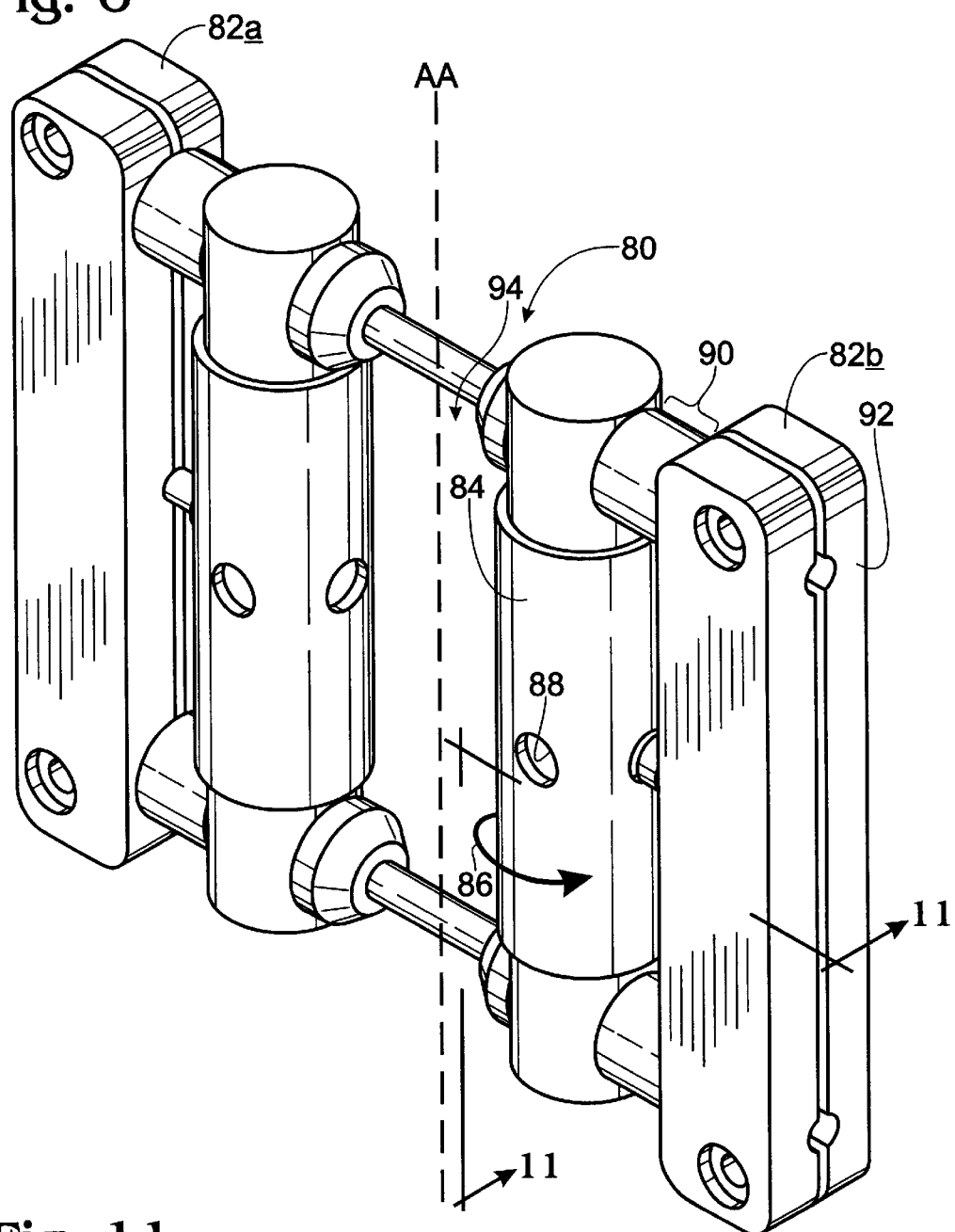
FIG. 6 is a perspective view of a buckle for use on a pelvic sling.

FIG. 6 shows a perspective view of a preferred buckle design for use on a pelvic sling. Buckle 80 is characterized by side-to-side symmetry relative to axis AA. Each of lateral buckle portions 82a and 82b is designed to engage and secure an end of sling extensions 56a and 56b, respectively, at an appropriate tension level. The details described below in relation to lateral buckle portions 82b are the same for lateral buckle portion 82a unless expressly distinguished.

Figure 7:
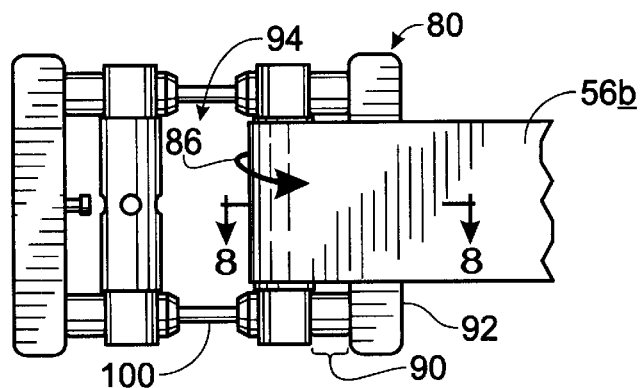
FIG. 7 is a partial front view of a sling showing one end portion of the sling engaging the buckle of FIG. 6.

Lateral buckle portion 82b includes rotating cylinder 84 that is free to rotate when buckle 80 is unlocked. As shown in FIG. 7, sling extension 56b wraps around cylinder 84. Cylinder 84 rotates in direction 86 when the sling is being tightened. Holes 88 are provided in cylinder 84, as shown in FIG. 6, for engaging a pin to lock rotation of cylinder 84 as described in more detail. Gap 90 is defined between cylinder 84 and side bar 92. Gap 90 is maintained by springs that are not shown in FIG. 11. As belt tension increases, cylinder 84 is pulled toward side bar 92, thereby decreasing gap 90. Eventually, a pin member extending from side bar 92 engages hole 88 in cylinder 84, causing rotation of cylinder 84 to lock. The surface of cylinder 84 is devised to frictionally hold and resist slipping of the belt material around cylinder 84 when rotation is locked.

Figure 8:
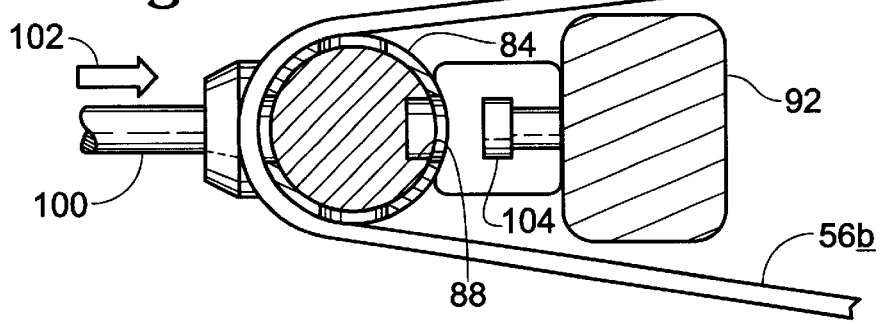
FIGS. 8–10 are cross-sectional views of the sling shown in FIG. 7, illustrating a preferred mechanism for locking the tension of the belt.
Figure 9:
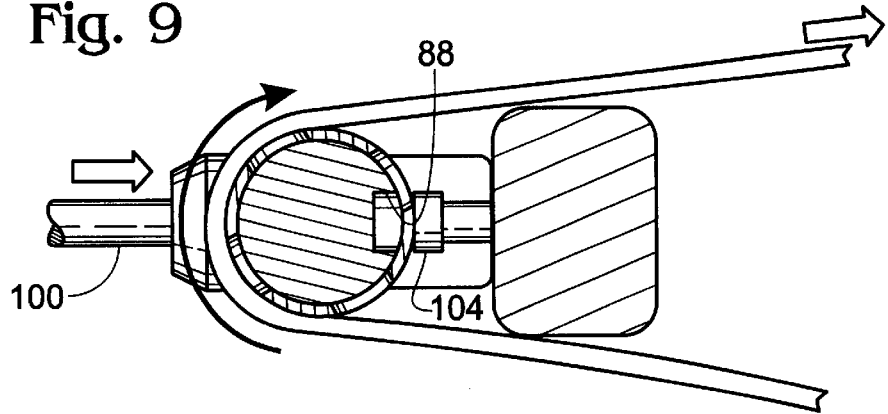
Figure 10:
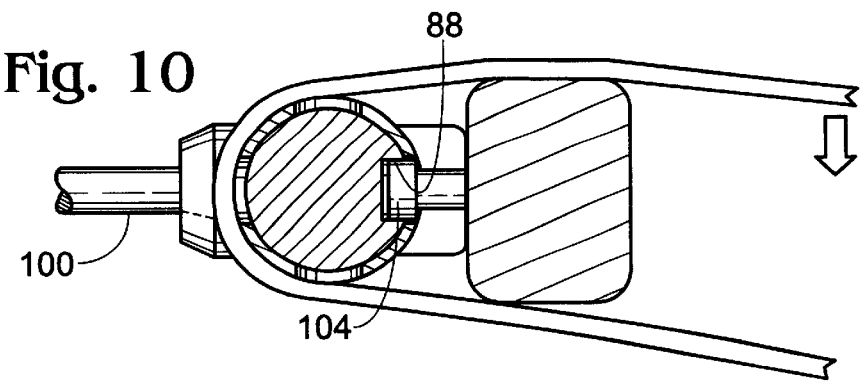

Buckle 80 is preferably comprised of reliable and robust design components to enable reproducible sling application to a preset and safe tension level. Sling extensions 56a and 56b are inserted through center portion 94 of buckle 80 and reverted by means of cylinders 84. Cylinders 84 have a rough outer surface to provide a high friction interface for engaging sling extensions 56a and 56b. Cylinder 84 rotates with low friction on a polyethylene roller core (not shown). The roller cores can slide laterally on parallel guide rods 100. FIGS. 8–10 show cross-sectional views through the sling of FIG. 7, illustrating the mechanism for locking rotational movement of cylinder 84. Lateral translation of cylinder 84 on guide rod 100 in direction 102 causes lock pin 104 to engage holes 88 in cylinder 84, disabling further rotation of cylinder 84. This in turn disables further sling tensioning due to the high friction interface between sling extension 56b and the outer surface of cylinder 84. This feature of the sling device automatically and reproducibly sets the tension of the sling at a predetermined level. The preset tensioning level is in the range of 150 N to 250 N, preferably 200 N.

Once the sling tension level is reached, lock pin 104 engages hole 88 on cylinder 84 and enters a second sinkhole of bigger diameter in cylinder 84. Lock pin 104 has a widened tip portion that engages the inner lumen of cylinder 84. Thus, even if the applied sling tensions decrease somewhat, cylinder 84 is not able to slide off lock pin 104, since cylinder 84 will impinge the widened tip portion of lock pin 104. Only if the applied sling tension decreases substantially will cylinder 84 be pushed off lock pin 104 by means of compression springs illustrated in FIG. 11. This design feature, referred to as "locking hysteresis," makes it possible to maintain the preset sling tension, even if the applied tension to the sling extensions decreases. An emergency technician can affix the ends of sling extensions 56a and 56b to the lateral sling portions without the need to maintain full sling tension for a prolonged amount of time, and without losing the preset sling tension.

Figure 11:
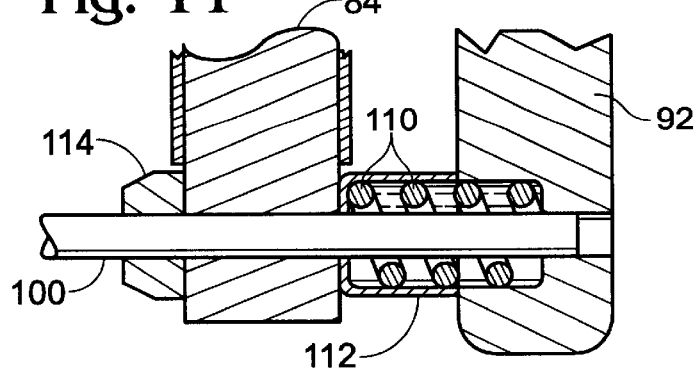
FIG. 11 is a partial cross-sectional view of the buckle shown in FIG. 6.

FIG. 11 shows another cross-section through buckle 80 of FIG. 7. Compression spring 110 counteracts lateral translation of cylinder 84 along guidepost 100. Compression spring 110 is mounted over guide rod 100, between side bar 92 and cylinder 84, and is covered by spring cage 112. This design component allows guided lateral translation of cylinder 84 against a pair of compression springs 110, only one of which is shown in FIG. 11. Collar 114 is located on the center region of guidepost 100. Collar 114 can plant rigidly to any site on guidepost 100 via screws. Collar 114 is used to hold each cylinder 84 in a laterally translated position, at which spring 110 is compressed to a preset value, for example 75 N for each compression spring. Therefore, cylinder 84 will maintain its position during sling tensioning up to the preset force value, while sling extensions 56a and 56b are pulled over the respective rotating cylinders. Only if the sling tension exceeds the preset value, will lateral translation of cylinder 84 be induced.

The sling buckle described above is fully symmetric, enabling sling buckle application in any orientation, therefore minimizing potential complications in its application. The sling buckle components are preferably designed to be fabricated from non-metallic, radiolucent materials, excluding the cylinders, lock pins, and compression springs. This enables radiographic examination while maintaining pelvic reduction and stabilization.

The sling design constitutes two distinct components, the sling and the sling buckle, which are combined in a functional unit with minimal effort. Different size-specific slings may be used with the same buckle. Furthermore, it may be desirable to provide a sling device in which the belt component is disposable and the buckle is reusable.

Sling Location

Figure 12:
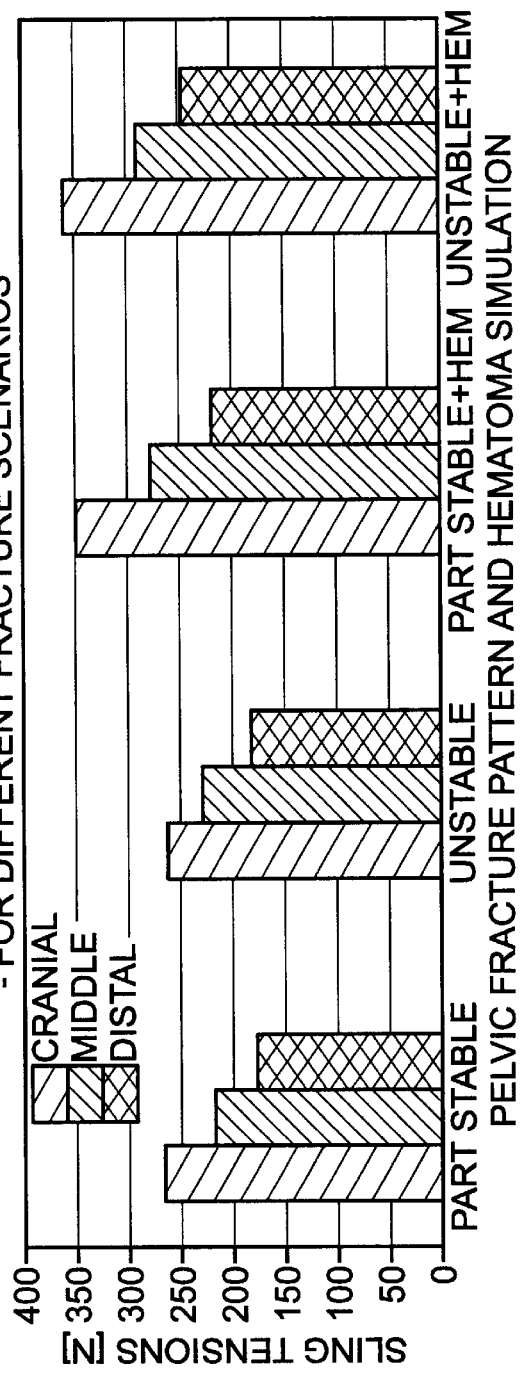
FIG. 12 is a graph illustrating the amount of tension required to reduce a fractured pelvis when the sling is applied at different locations.

An optimal sling location has been found to be within a transverse plane at the level of the greater trochanteric region, just proximal of the pubis symphysis. Application of a sling further distally is not feasible from a clinical perspective, disabling vital access to rectal and genital regions and the femoral artery. Application of a sling further proximally results in a significant decrease in the amount and quality of pelvic reduction corresponding to constant amounts of sling tension. FIG. 12 is a bar graph showing the results of an experiment to determine which sling location required the least sling tension to achieve pelvic reduction in different fracture scenarios. The graph shows that distal sling application, i.e., at the level of the acetabulum, required the least sling tension to achieve pelvic reduction in each of four different fracture scenarios: partially stable, unstable, partially stable and hemorrhaging, unstable and hemorrhaging.

Sling Tension

Figure 13:
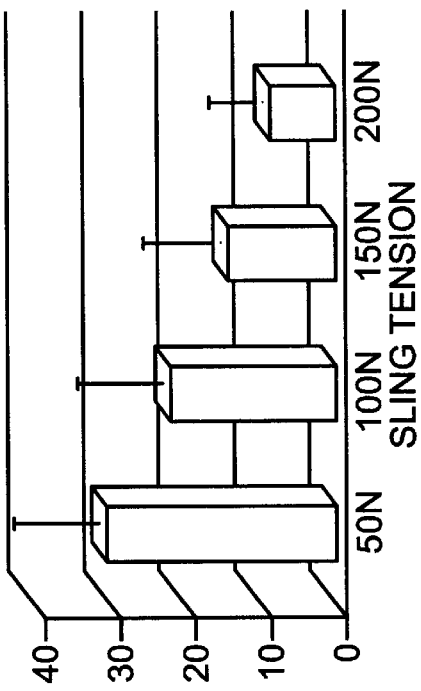
FIG. 13 is a bar graph illustrating the results of an experiment to determine the amount of sling tension required to adequately reduce the symphysis gap in a fractured pelvis.
Figure 14A:
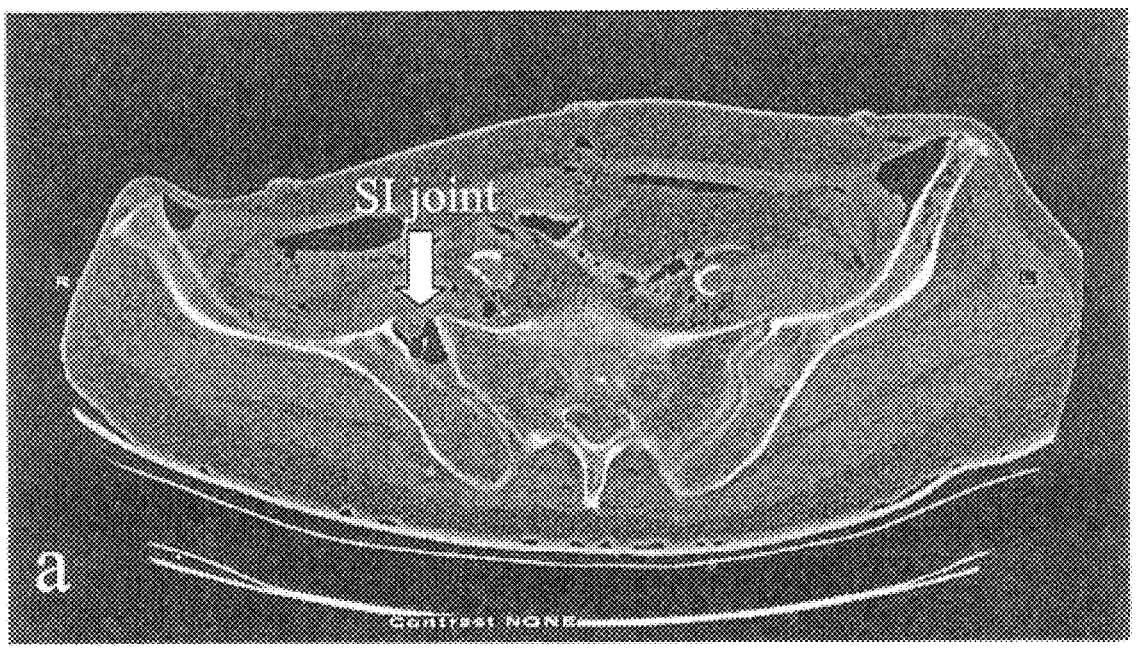
FIG. 14 is a set of four CT images showing a fractured pelvis before and after sling-induced reduction.
Figure 14B:
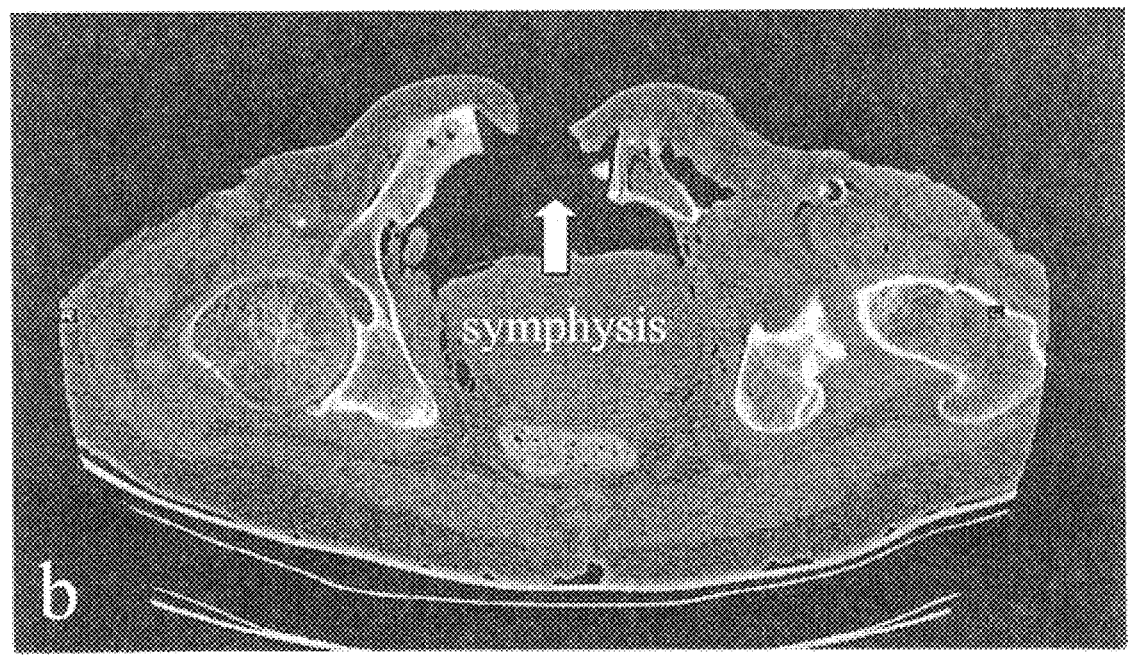
Figure 14C:
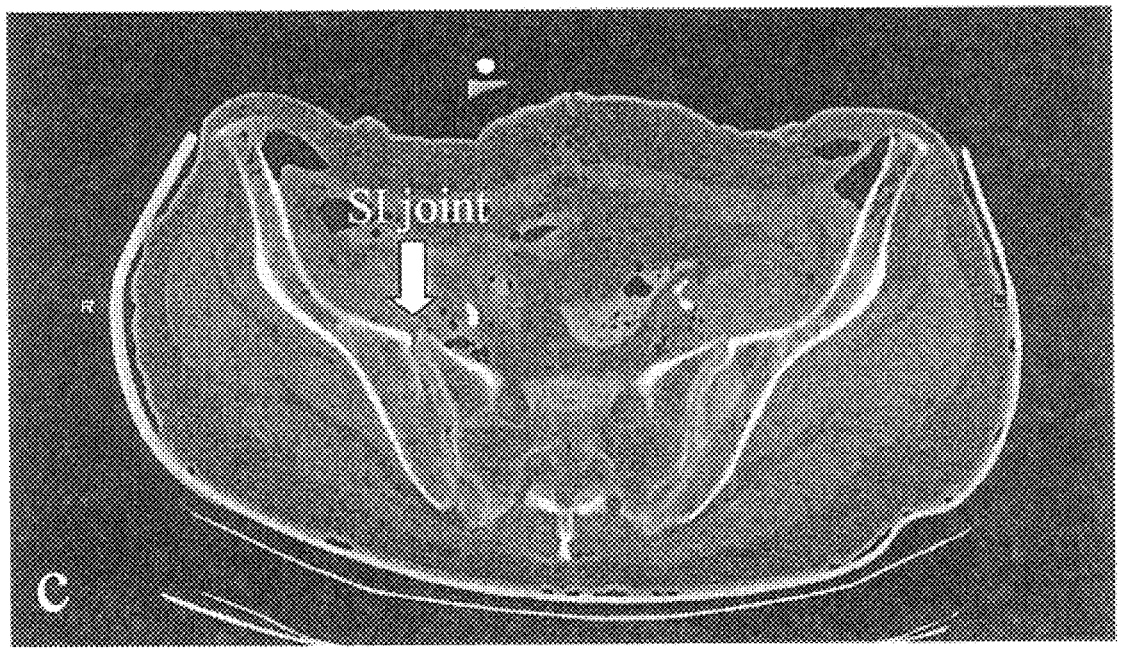
Figure 14D:
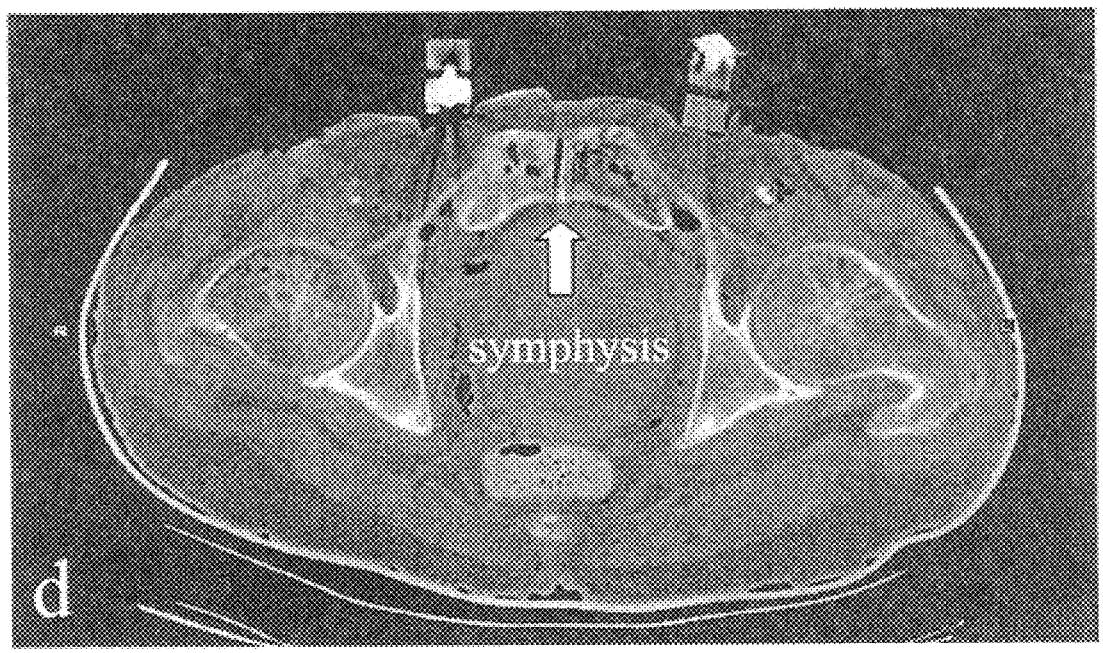

FIG. 13 shows a bar graph illustrating the results of an experiment to determine the relationship between sling tension and symphysis gap reduction. A sling tension level of 200 N was required to reduce the pelvis sufficiently, i.e., symphysis gap of less than 10 nmm.

FIG. 14 shows four CT images of a fractured pelvis. Figures A and B show the fractured pelvis prior to sling-induced reduction. The pelvic ring disruption is apparent by a widened SI joint in image (A) and a symphysis gap of 50 mm (B). As shown in images C and D, sling tension at the acetabular level at a tension of 200 N resulted not only in the most efficient translation of the applied sling tension into pelvic reduction, but also yielded the best quality in reduction.

Although the invention has been disclosed in its preferred forms, the specific embodiments thereof as disclosed and illustrated herein are not to be considered in a limiting sense, because numerous variations are possible. As used herein, singular terms do not preclude the use of more than one of the associated element, and embodiments using more than one of a particular element are within the spirit and scope of the invention. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A sling device for stabilizing a fractured hip comprising a belt member having two end portions, and a buckle having two substantially identical belt-engaging mechanisms, each belt-engaging mechanism being configured to receive an end portion of the belt member so that the belt member can be tightened symmetrically around a person's pelvis by pulling on the end portions of the belt member simultaneously, wherein each belt-engaging mechanism has a spring biased cylinder that is free to rotate until sufficient pressure is applied to the cylinder at which point a pin engages a recess in the cylinder thereby stopping further rotation of the cylinder.

2. The sling device of claim 1, wherein each belt-engaging mechanism automatically locks tightness of the belt member at a force level in the range of approximately 150 N to 250 N.

3. The sling device of claim 2, wherein each belt-engaging mechanism automatically locks tightness of the belt member at a force level in the range of approximately 200 N.

4. The sling device of claim 1, wherein the belt member is radiolucent.

5. The sling device of claim 1, wherein each belt engaging mechanism exhibits a locking hysteresis effect so that the amount of force required to lock rotation of the cylinder is substantially greater than the maximum force level required to free rotation of the cylinder.

6. The sling device of claim 1, wherein each belt-engaging mechanism includes a rotating cylinder having an outer surface for contacting a portion of the belt member that at least partially wraps around the cylinder, wherein the belt portion frictionally grips the outer surface of the cylinder so that when rotation of the cylinder is locked the belt member is prevented from slipping around the outer surface of the immobilized cylinder.

7. The sling device of claim 1 wherein each belt-engaging mechanism is configured to automatically set the belt at a tension level that has been predetermined to substantially reduce the fractured pelvis without excessive compression.

* * * * *